United States Patent [19]

Grinninger

[11] 4,244,825

[45] * Jan. 13, 1981

[54] BROMINATED CINNAMALACETOPHENONE

[75] Inventor: Lowell D. Grinninger, Hoffman Estates, Ill.

[73] Assignee: PPG Industries, Inc., Pittsburgh, Pa.

[ * ] Notice: The portion of the term of this patent subsequent to May 15, 1996, has been disclaimed.

[21] Appl. No.: 43,581

[22] Filed: May 29, 1979

[51] Int. Cl.³ ............................................... C09K 3/28
[52] U.S. Cl. ................................ 252/8.1; 106/18.24; 428/921; 521/87
[58] Field of Search ........................... 521/87; 252/8.1; 106/18.24

[56] References Cited

U.S. PATENT DOCUMENTS

| | | | |
|---|---|---|---|
| 3,766,136 | 10/1973 | Howell et al. | 260/45.7 RL |
| 4,154,765 | 5/1979 | Grinninger | 260/592 |

Primary Examiner—Richard D. Lovering
Attorney, Agent, or Firm—Edward J. Whitfield

[57] ABSTRACT

A novel mixture of brominated cinnamalacetophenones is provided said mixture consisting essentially of from about 80 to 90 percent by weight chain brominated cinnamalacetophenone tetrabromide, from about 5 to about 10 percent by weight chain brominated cinnamalacetophenone dibromide and from about 5 to about 10 percent by weight di-ring brominated cinnamalacetophenone hexabromide.

1 Claim, No Drawings

BROMINATED CINNAMALACETOPHENONE

BACKGROUND OF THE INVENTION

Self-extinguishing properties are imparted to organic polymer compositions that are normally susceptible to burning by incorporating in the polymer composition a brominated arylidene ketone is described, for example, in U.S. Pat. No. 3,766,136. One of the more effective brominated arylidene ketones described in said patent is cinnamalacetophenone tetrabromide.

The method described in Example VIII of said patent for preparation of cinnamalacetophenone tetrabromide produces commercially unsatisfactory low yields of crude product and in addition the crude product requires additional processing to remove undesirable color imparting impurities.

SUMMARY OF THE INVENTION

A novel mixture of brominated cinnamalacetophenones is provided said mixture consisting essentially of from about 80 to about 90 percent by weight chain brominated cinnamalacetophenone tetrabromide, from about 5 to about 10 percent byy weight chain brominated cinnamalacetophenone dibromide and from about 5 to about 10 percent by weight di-ring brominated cinnamalacetophenone hexabromide.

The mixture of brominated cinnamalacetophenones of this invention may be represented as follows:

I. From about 80 percent to 90 percent of weight on weight of mixture of:

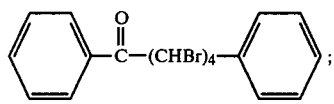

II. From about 5 percent to 10 percent by weight on weight of mixture of:

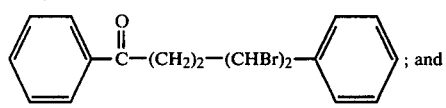
; and

III. From about 5 percent to 10 percent by weight on weight of mixture of:

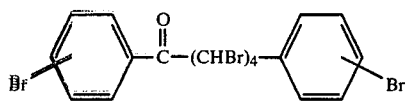

DESCRIPTION OF THE INVENTION

This invention provides a noval mixture of brominated cinnamalacetophenones, said mixture consisting essentially from about 80 to 90 percent by weight chain brominated cinnamalacetophenone tetrabromide, from about 5 to 10 percent by weight chain brominated cinnamalacetophenone dibromide and from about 5 to about 10 percent by weight of di-ring brominated cinnamalacetophenone hexabromide.

The mixture of brominated cinnamalacetophenones of this invention have been found to be at least as effective as pure cinnamalacetophenone tetrabromide in imparting self-extinguishing properties to organic polymer compositions.

The mixture of brominated cinnamalacetophenones of this invention is prepared by brominating cinnamalacetophenone suspended in a saturated linear aliphatic or cycloaliphatic liquid hydrocarbon. The brominated cinnamalacetophenone mixture as isolated from the reaction mixture, ranges in color from white to a pale greenish yellow, thus enabling use of the product in, for example, white or lightly colored plastic compositions without further purification.

The saturated linear aliphatic hydrocarbons used as the reaction medium are straight-chained and may have from about 6 to about 12 carbon atoms. Preferably, however, the number of carbon atoms will be from about 6 to about 8. Hexane and heptane are especially preferred among the linear hydrocarbons so defined.

The saturated cycloaliphatic hydrocarbons are the preferred reaction media and may have from about 5 to about 8 carbon atoms. Cyclohexane is especially preferred. A charge of this hydrocarbon may be used repeatedly without rectification in the batch-wise bromination of cinnamalacetophenone. Moreover, such an advantage may be utilized in a continuous operation of the method of this invention.

It will be readily apparent to those skilled in the art that mixtures of the above-designated hydrocarbons may be used.

The temperature at which the bromination reaction is carried out in the hydrocarbon medium may range from about 0° C. to about 80° C. but the preferred range is from about 20° C. to about 60° C. When cyclohexane is used as the reaction medium the preferred temperature is from about 20° C. to about 30° C.

The relative amounts of reaction medium and cinnamalacetophenone may be adjusted to facilitate mixing of the slurries encountered but a weight ratio of hydrocarbon to the reactant within the range of about 5:1 to about 20:1 is usually satisfactory.

A further discovery has been made in connection with the recycling of a cyclohexane reaction medium as a mother liquor in the preparation of subsequent batches of the brominated product, namely, that from about 98% to about 99.5%, by weight, of the stoichiometric amount of bromine (that amount which combines with cinnamalacetophenone to form cinnamalacetophenone tetrabromide) may be used in alternating batches to give excellent and reproducible yields of product having a high melting point and, in particular, good color. Thus, a stoichiometric amount of bromine may be used in the odd-numbered batches of a series while the reduced amount is employed in the even-numbered batches. The purpose of the reduced amounts of bromine is to compensate for the unreacted bromine which may remain in the mother liquor from a preceding batch and thus it will be understood that a strict adherence to the alternating routine is not always necessary. Observation of the mother liquor may indicate that the bromine content is such that the routine should be interrupted until the optimal conditions are re-established. The alternating routine is preferred, however, because of its simplicity and consistency in affording good results.

The time allotted for the physical step of introducing the bromine into a suspension of cinnamalacetophenone in the hydrocarbon is not particularly critical but it is usually complete in about 0.5 hour. Likewise, the holding time after all of the bromine has been introduced is not critical; it may be governed by the color of the reaction mixture but a period of from 45 minutes to one hour is usually sufficient.

The mixture of brominated cinnamalacetophenones of this invention may be incorporated into the polymer by techniques known to the art, such as for example, mixing in conventional blending equipment and extruding the melt into pellets.

The mixture of brominated cinnamalacetophenones of this invention are incorporated into the polymer in an amount sufficient to impart self-extinguishing properties to the polymer, typically from about 0.1 percent to about 10 percent based on weight of polymer.

The mixture of brominated cinnamalacetophenones of this invention may be used to impart self-extinguishing properties to both foamed and unfoamed polymers, such as polyalphaolefins, e.g., polypropylene and the like or polyvinylaromatics, e.g., polystyrene and the like.

The invention is further illustrated but it is not intended to be limited by the following examples.

EXAMPLE 1

Cinnamalacetophenone (35.1 parts, 0.15 mole) is added to about 200 parts of heptane and the resulting slurry is stirred while being heated to about 55° C. before the introduction of 48 parts (0.3 mole) of bromine is commenced. The exotherm of the bromination reaction raises the temperature to about 60° C. during the 23 minute introduction period. The mixture is stirred at 50°–60° C. for about 80 minutes and then it is cooled and filtered. The filter cake and reaction vessel are washed with about 70 parts of heptane. After drying, 63.1 parts (75% of theory) of a satisfactory product are recovered. The pale greenish-yellow product metals at 161.5°–167.5° C.

EXAMPLE 2

Cinnamalacetophenone (35.1 parts, 0.15 mole) is slurried with about 230 parts of cyclohexane at 55° C. while the introduction of 48 parts (0.3 mole) of bromine is started. A temperature of from about 50° C. to about 60° C. is maintained by the exotherm of the bromination. After about one-half of the bromine is in, the reaction mixture becomes a clear solution but precipitation occurs shortly thereafter. The introduction of bromine is completed in a total time of about 40 minutes. A thick slurry of fine particles is obtained but stirring is continued for about one hour. The slurry is cooled and filtered, and the filter cake is washed once with about 100 parts of cyclohexane. The filter cake is dried to give 57.5 parts (69% of theory) of a satisfactory product which melts at 159.5°–165.5° C. Infra-red analysis indicates that about 88% of the product is the tetrabromide and the remainder is made up of approximately equal parts of the dibromide and hexabromide. Elemental analysis of the product shows that it contains 57.27% bromine whereas the theoretical value for the tetrabromide is 57.7%.

EXAMPLES 3–6

A series of batches of brominated cinnamalacetophenone is prepared according to the general procedure of Example 2 except that the temperature is maintained within the range of 20° C. to 30° C. throughout the reaction, the reaction medium (550 parts of cyclohexane in Example 3) is recycled as a mother liquor after adjustment for losses, and the weight of bromine in Examples 4 and 6 is 1% less than the stoichiometric amount (48 parts) used in Examples 3 and 5. The yields, colors, and melting points of the products are given in Table 1.

TABLE I

| Example No. | Yield (%) | Color | M.P. (°C.) |
| --- | --- | --- | --- |
| 3 | 65.8 | slightly off-white | 167–169 |
| 4 | 81.7 | faintly greenish-white | 155–165 |
| 5 | 82.0 | faintly yellowish-white | 162–168 |
| 6 | 85.4 | faintly yellowish-white | 162–168 |
| Average | 78.7 | — | — |

EXAMPLE 7

A slurry of 35.1 parts (0.15 mole) of cinnamalacetophenone in about 550 parts of cyclohexane is stirred while the introduction of 48 parts (0.3 mole) of bromine is commenced. The temperature of the reaction mixture is maintained between 20° C. and 30° C. for 0.5 hour while the bromine is introduced. When about half of the bromine is in, the reaction mixture becomes a clear red solution; the solution is seeded with 0.25 part of cinnamalacetophenone tetrabomide and the remainder of the bromine is charged into the reaction vessel. Precipitation begins shortly thereafter and the slurry is stirred for about 30 minutes before it is filtered. The vessel and filter cake are washed twice with 40 part portions of cyclohexane. After drying, 48.6 parts (58.4% of theory) of yellowish-white crystals melting at 163°–168° C. are obtained.

EXAMPLES 8–16

The general procedure of Example 7 is repeated in a series of preparations but the mother liquor of each preceding batch is used as the reaction medium in the succeeding batch instead of "virgin" cyclohexane, e.g., the mother liquor from Example 7 is the reaction medium in Example 8. The yields and melting points of the products are listed in Table II.

TABLE II

| Example No. | Yield (%) | M.P. (°C.) |
| --- | --- | --- |
| 8* | 71.9 | 155.5–158.5 |
| 9* | 76.6 | 160–164 |
| 10* | 79.7 | 153–161 |
| 11* | 91.6 | 148.5–153.5 |
| 12 | 90.5 | 150–155 |
| 13* | 102.0** | 146.5–156.5 |
| 14* | 79.8 | 154–158 |
| 15* | 74.4 | 144–152 |
| 16* | 91.8 | 148.5–159.5 |

*Br₂ used is 99% of stoichiometric amount of Br₂ required for tetrabromide.
**The apparently anomalous yield is caused by precipitation of an extraordinary amount of di-and hexabromides when the mother liquor becomes super-saturated with solute.

The yields of brominated cinnamalacetophenone from Examples 7 through 16 average 81.7% and a blend of the products melts at 151°–158° C.

EXAMPLE 17

Two polystyrene compositions were prepared one of which contained 0.5 weight percent of the brominated cinnamalacetophenone mixture prepared in Example 2, while the other contained 0.5 weight percent of pure tetrabromo cinnamalacetophenone.

The limiting Oxygen Index (LOI) of each polystyrene composition was determined according to ASTM D-2863-70. The LOI of polystyrene incorporating the brominated cinnamalacetophenone mixture of the invention was 30.0, whereas the LOI of polystyrene incorporating pure tetrabromo cinnamalacetophenone was 29.5.

Although the invention has been described herein with particular reference to preferred embodiments thereof it is apparent that many variations may be made therein by those skilled in the art without departing from the spirit and scope of the invention.

I claims:

1. A composition particularly suited for imparting self-extinguishing properties to organic polymers, said composition consisting essentially of a mixture of from about 80 percent to 90 percent by weight on weight of mixture of chain brominated cinnamalacetophenone tetrabromide, from about 5 percent to 10 percent by weight on weight of mixture of chain brominated cinnamalacetophenone dibromide and from about 5 percent to about 10 percent by weight on weight of mixture of di-ring brominated cinnamalacetophenone hexabromide.

* * * * *